United States Patent [19]

Ninan et al.

[11] Patent Number: 4,825,875

[45] Date of Patent: May 2, 1989

[54] COMPUTER LOCALIZATION IN PRESSURE PROFILE

[76] Inventors: Champil A. Ninan; Abraham C. Ninan, both of 453 Morningside Dr., Fayetteville, N.C. 28101

[21] Appl. No.: 111,683

[22] Filed: Oct. 23, 1987

[51] Int. Cl.$^4$ .............................................. A61B 5/10
[52] U.S. Cl. ..................................... 128/748; 128/774
[58] Field of Search ............... 128/774, 780, 782, 748, 128/733, 642

[56] References Cited

U.S. PATENT DOCUMENTS

| | | | |
|---|---|---|---|
| 4,052,892 | 10/1977 | Browne | 128/748 X |
| 4,063,548 | 12/1977 | Klatt et al. | 128/748 X |
| 4,191,196 | 3/1980 | Bradley et al. | 128/748 X |
| 4,217,911 | 8/1980 | Layton | 128/748 |
| 4,233,991 | 11/1980 | Bradley et al. | 128/748 X |
| 4,407,301 | 10/1983 | Streisinger | 128/774 |
| 4,459,990 | 7/1984 | Barnea | 128/656 |
| 4,484,585 | 11/1984 | Baier | 128/748 |
| 4,538,621 | 9/1985 | Jarczyn | 128/748 |
| 4,539,640 | 9/1985 | Fry et al. | 128/734 X |
| 4,566,465 | 1/1986 | Arhan et al. | 128/774 X |
| 4,587,972 | 5/1986 | Morantte | 128/629 X |

OTHER PUBLICATIONS

Benign Prostatic Hypertrophy; Edited By: Frank Hinman, Jr., Publisher: Springer-Verlag, N.Y.-1983, Chapters 54, 55, and 56.
Campbell's Urology; (Chapter 72), Fifth Edition, W. B. Saunders Company, 1986.

Primary Examiner—Max Hindenburg
Assistant Examiner—Angela D. Sykes

[57] ABSTRACT

This invention is to enable exact localization and display of the part being examined in graphic form. When doing an endoscopic examination the exact location of the treatment or examining element can be determined in relation to anatomical landmarks. This is particularly useful in one of the Urodynamic tests called Urethral Pressure Profile. The pressure being measured along the urethra can be correlated exactly with visible anatomical landmarks. Visible landmarks is stressed because during surgery the operating surgeon relies on visible landmarks to decide how much tissue needs to be removed. The results can be displayed, analyzed, interpreted, stored and printed. The same can be done with any other organ.

14 Claims, 3 Drawing Sheets

COMPUTER LOCALIZATION IN PRESSURE PROFILE

BACKGROUND OF THE INVENTION

According to co-patent application No. 815455 now, U.S. Pat. No. 4,742,815 titled 'Computer Monitoring of Endoscope' by the same authors, tranducers were mounted on an endoscope to monitor its movements in various planes. Thus the treatment or examining part of the endoscope can be monitored, displaying its exact position in relation to landmarks in the organ being examined.

A further important application of the said monitoring system is in a Urodynamic test called Urethral Pressure Profile. In this test the pressure along the Urethral passage from the bladder to the outside is measured and recorded as a graphic curve. According to present art in an attempt to correlate pressure with length, a motor is used to withdraw the catheter at a fixed rate while fluid is injected continuously at a fixed rate, U.S. Pat. Nos. 4,191,196 and 4,233,991. Distance transversed by the pressure recording catheter can be computed. Catheters are made to measure pressure in the bladder and simultaneously in the urethra, U.S. Pat. Nos. 4,407,301, 4,484,585, and 4,538,621. However, when such a recording is made there is no way to make exact correlation with pressure and endoscopically visible landmarks. Even in Cystometry System described in U.S. Pat. No. 4,217,911, exact correlation is not possible. At present electromyographic recordings are made with pressure, U.S. Pat. No. 4,063,548, but this too does not give exact relationship to visible anatomical landmarks.

It is the purpose of this invention to correlate pressures with exact endoscopically visible anatomical sites within the organ, to graphically display, store, print and or perform other actions depending on the data received by a microcomputer.

In disease obstruction can occur at the bladder neck, in the prostatic urethra or anywhere along the said urinary passage. The exact site of obstruction can be determined by means of this invention. Tests described in this invention can be performed during surgery to ensure complete removal of the obstructing tissue. Exact site of the sphincter in relation to endoscopically visible anatomical landmarks can also be located.

If pressure testing reveals cause of obstruction is non coordination of external sphincter then surgery is not needed.

BRIEF DESCRIPTION OF DRAWINGS

The above mentioned purpose and descriptions of the invention will be clear by reference to the following drawings wherein.

DETAILED DESCRIPTION OF THE PREFERRED EMBODIMENT

Description will follow under the following headings:

Description of the organ being examined—ORGAN.
Description of the apparatus—APPARATUS.
Functioning of the apparatus—PROCEDURE.
Computer programming principles—COMPUTER.

This invention can be used to locate abnormalities in various organs. As an example we have selected bladder and urinary passage.

ORGAN

Figure 1:
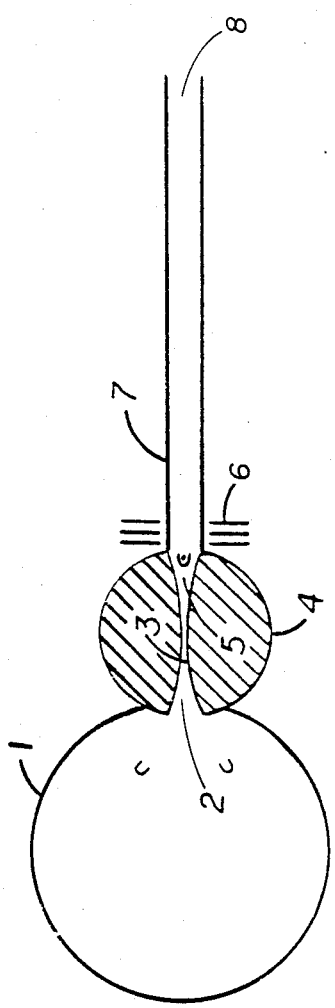
FIG. 1 shows the human male urinary bladder and passage.

FIG. 1 shows the diagram of a male urinary bladder and urinary passage. The bladder 1, temporarily stores urine and periodically expells it when the bladder neck 2, opens as the bladder 1, contracts. Urine passes through the prostatic urethra 3, which is completely surrounded by the prostate 4. The distal limit of the prostate is marked by a small projection called the verumontanum 5. This is a most important landmark because just distal to the verumontanum 5, is the external urethral sphincter 6, which relaxes soon after the urination process begins. Beyond this is the urethra 7, affording a free passage of urine to the outside beyond the external urethral meatus 8.

APPARATUS

Figure 2:
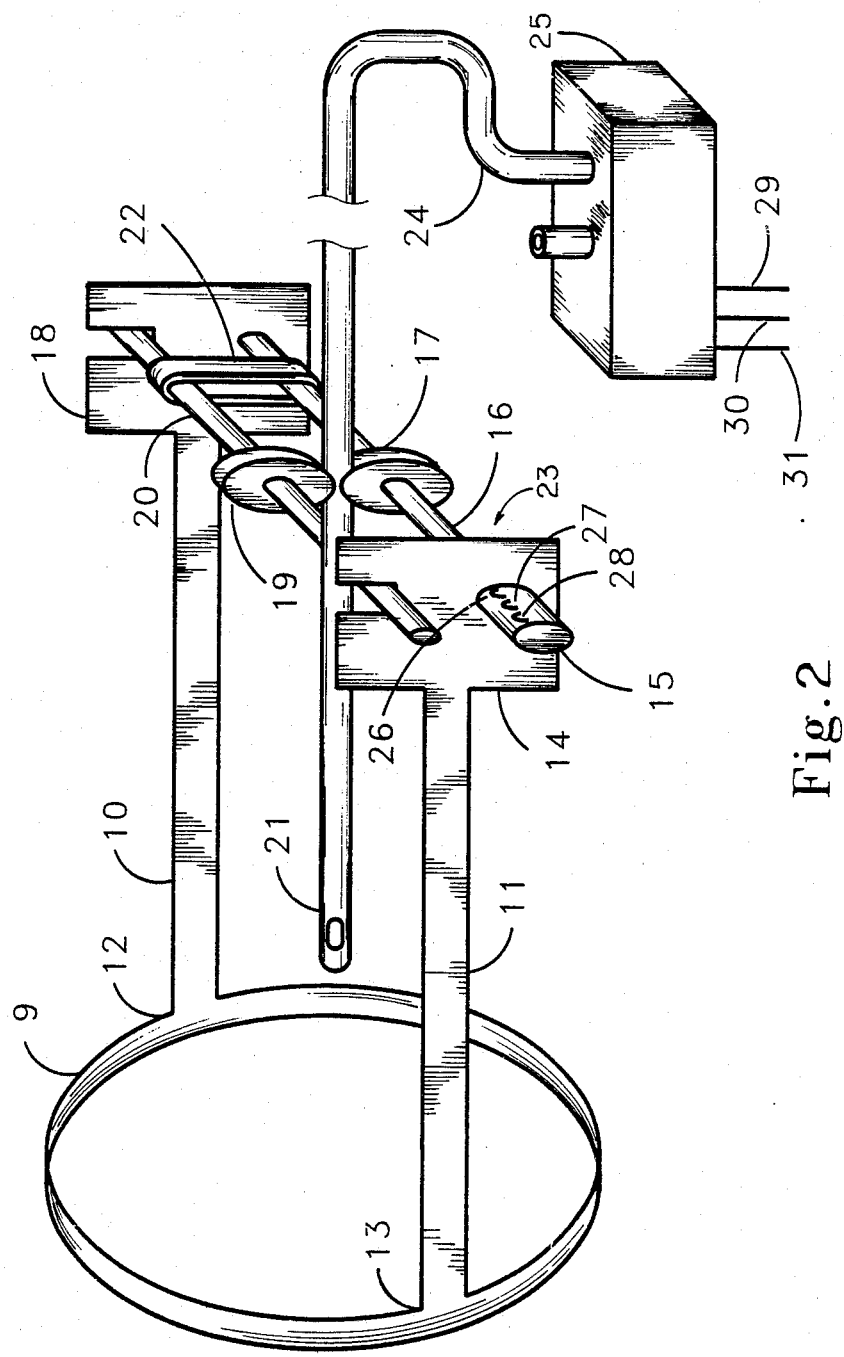
FIG. 2 is a view of the apparatus used in this invention.
Figure 3:
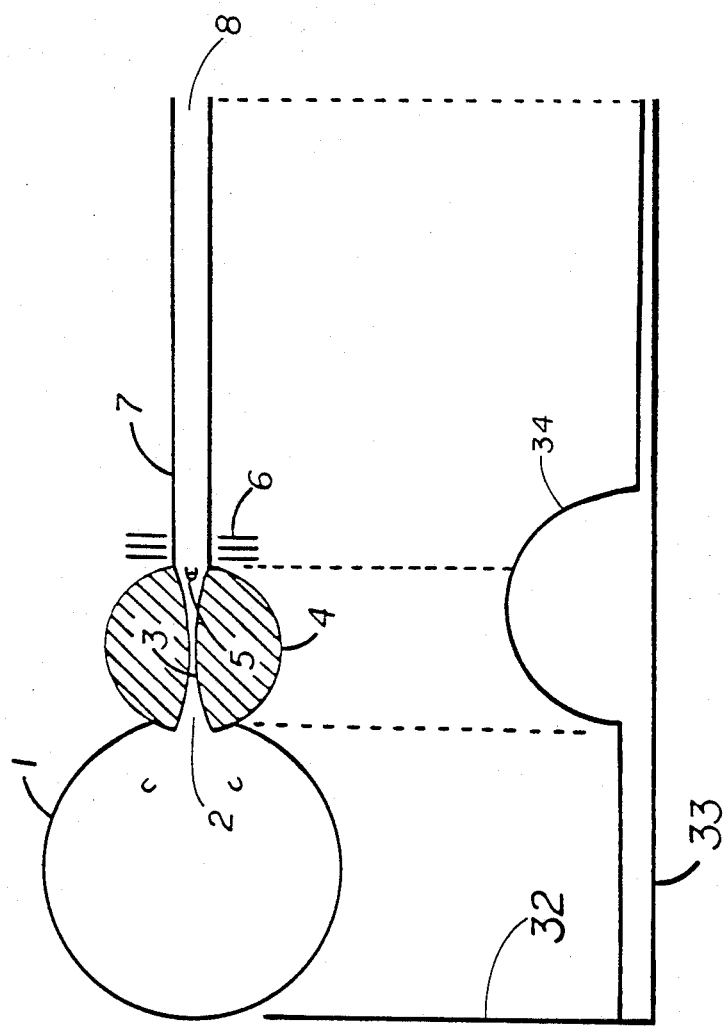
FIG. 3 is a graphic display of a male bladder and urinary passage with simulated pressure recording in exact relation to landmarks.

One way to accomplish the objectives of this invention is by using the apparatus displayed in FIG. 2. A ring 9, is attached to the patient's body, not shown, to provide a fixed reference point. Two arms 10, and 11, one ends of each 12 and 13, are attached to the ring 9. Between the distal ends 14 and 18 is attached a transducer 15 and its rotating shaft 16 which goes through a grooved wheel 17. The circumference of the wheel 17, is at least 1/10th of the length of the passage being examined because the transducer 15, used here is a potentiometer with 10 turns. This is obtainable from any electronic component store. Another grooved wheel 19, is just above wheel 17, and is held in place by shaft 20, which is fixed to distal ends 14 and 18, of arms 11 and 10, respectively. The space between wheels 17, and 19 is for the passage of an endoscope, a catheter 21, or a probe. Rubber rings 22 and 23 (not visible), are to keep the wheels 17 and 19, tightly in contact with the catheter 21, so that as the catheter 21, moves in and out of the patient's body the wheels 17 and 19, will turn without slipping. The proximal end 24, of catheter 21, is attached to a pressure transducer 25, obtainable from Omega Engineering, Inc., One Omega Drive, P. O. Box 4047, Stamford, CT 06907.

Electrical connections are made from three pins 26, 27, and 28, of transducer 15, and three pins 29, 30 and 31 of pressure transducer 25. Pins 26 and 29, are connected to +12 volts supply which is derived from the microcomputer, not shown. Microcomputer used here is an Apple, Model IIe (enhanced), obtainable from Apple Computer, 20525 Mariani avenue, Cupertino, California 95014. Pins 27 and 30, are connected to ground of the said microcomputer. Pin 28 is output of transducer 15, and pin 31, gives output from pressure transducer 25. These two outputs 28 and 31, are connected to an analog to digital converter card, not shown, that is plugged into a slot, not shown, inside the microcomputer.

PROCEDURE

Calibration of the transducer 15, is done by passing a catheter 21, between wheels 17 and 19, a known distance. Similarly the pressure transducer 25, is calibrated by applying a known pressure and taking computer readings.

The first thing to do after calibration is to establish the landmarks and fix it in the microcomputer memory. In this case the landmarks are the bladder neck 2, and the verumontanum 5. The transducer 15, is set to its highest reading by turning the wheel 17, counterclockwise. Then a cystoscope, preferably a flexible cystoscope is passed between wheels 17 and 19, and then through the external urethral meatus 8, into the bladder 1. The cystoscope is then withdrawn. When the bladder neck 2 is reached the 'open apple' key of the microcomputer is pressed. The reading from transducer 15, will then be stored in memory as being the location of the bladder neck. As the cystoscope is withdrawn and when the verumontanum 5, is reached, the 'open apple' key is again depressed. The reading of transducer 15, is taken and stored in memory as being the location of the verumontanum 5. Upon further withdrawal of the cystoscope the external urethral meatus 8 will finally be reached. In a similar fashion this is also marked in memory by pressing the 'open apple' key.

Fixing of landmarks can also be performed in many ways. For example ultrasound display of prostate will enable localization of upper and lower limits of prostate which is bladder neck 2 and level of the verumontanum 5 respectively. XRay display means will also accomplish the same.

The next step is to draw the bladder and urethra on the computer display screen. The distance between bladder neck 2, and verumontanum 5, is computer. The prostate 4, and prostatic urethra 3, are drawn according to measurement taken and stored in memory. Next the bladder 1, is drawn. Since size of the bladder 1, is variable and not important, it is drawn 2.5 times the size of the prostate 4. The rest of the urethra 7, is then drawn up to the external urethral meatus 8. The length of the urethra 7, being exactly according to measurement taken intitially.

Transducer 15, is again set to its maximum reading by turning wheel 17, counter clockwise. A catheter 21, is then passed into the bladder. Moving this catheter 21 in and out will vary computer readings from transducer 15. Since anatomical positions were marked and stored in memory, position of the tip of the catheter 21, will be known and will be displayed.

Graphic display of the pressure at corresponding points along the urinary tract is shown below the figure of the bladder and urethra just drawn on the computer screen. A vertical line 32, representing 'Y' axis is drawn below the end of the bladder. Below this is a horizontal line 33, representing 'X' axis is drawn.

As the catheter 21 is moved, a dot is drawn. Its position in the 'Y' axis is dependent on the pressure recorded from transducer 25. 'X' axis of the dot depends on the reading obtained from transducer 15, and displays exact location along the urinary passage. As the catheter 21 is withdrawn pressure along its passage is graphically displayed 34. In one mode of this test according to present art water is injected into the catheter at a fixed rate and pressure is simultaneously recorded.

Interpretation can easily be programmed. The computer stores and prints the display.

COMPUTER

The first time 'open apple' key is depressed, a reading of the transducer 15 is taken and assigned to variable BN, which represents bladder neck 2. Next when the 'open apple' is depressed value is similarly assigned to variable UV, which represents verumontanum 5. The third time 'open apple' is pressed the external urethral meatus 8, is marked as EM.

The computer is switched to high resolution graphics page. A circle is drawn, in the upper half of the screen, to represent the prostate 4 with radius being $PR=(VM-BN)/2$. Then the bladder 1 is drawn with radius $BR=2.5 * PR$. The urethra 7 is drawn from VM to EM.

Y axis 32 and X axis 33 lines are drawn in the lower half of the screen.

Memory locations of transducers 15 and 25 are peeked and these form the X and Y axis for the dot to be plotted. After plotting is completed then this is saved in the computer disc in the patient's file. For printing a screen dump program is used.

What is described is one method of accomplishing the objects of the invention. Other methods are possible once the principles are understood. This invention is not limited by the illustration presented but is within the scope of the following claims.

What is claimed are:

1. A method of precise anatomical profilometry utilizing profile apparatus joined to a computer having a memory and video screen, said computer communicating with a scope means and catheterizing means, the steps comprising:
   (a) fixing an anatomical reference point in the computer memory by internal insertion of the scope means in the selected anatomical region,
   (b) displaying the region graphically while simultaneously displaying a reference axis on the screen,
   (c) inserting the catheterizing means into the anatomical region, and
   (d) graphically representing the pressure applied to the catheterizing means and its position on the screen in exact location relative to the anatomical region displayed.

2. The method of claim 1 wherein the step of fixing an anatomical reference point with a scope means comprises fixing a reference point endoscopically.

3. The method of claim 2 and including fixing a second anatomical reference point.

4. The method of claim 1 wherein the step of fixing an anatomical reference point with a scope means comprises fixing a reference point cystoscopically.

5. The method of claim 1 wherein displaying the anatomical region comprises the step of displaying the region in graphic form on the computer screen above the reference axis.

6. The method of claim 1 wherein the step of displaying an anatomical region comprises drawing the anatomical region on the video screen.

7. The method of claim 6 and including the step of drawing one part of the anatomical region in disproportionate dimension to another part of the anatomical region.

8. The method of claim 1 wherein graphically displaying the anatomical region comprises the step of drawing a bladder and urethra on the video screen.

9. The method of claim 1 wherein the step of graphically representing the catheterizing means on the screen comprises the step of moving the catheterizing means in and out of the anatomical region.

10. The method of claim 1 and including the step of fixing a reference point on the patient's body by attaching the apparatus thereto.

11. A method of precise urethral profilometry utilizing profile apparatus joined to a computer with memory, a video screen and a keyboard, said computer in communication with a first spatial sensitive transducer, a second pressure sensitive transducer, scope means and a catheterizing means, the method comprising the steps of:
(a) attaching the apparatus to the patient's body to provide a fixed reference point,
(b) calibrating said transducers,
(c) fixing anatomical reference points in the computer memory by:
 (1) setting the first transducer to an initial reading,
 (2) passing the scope means into the bladder through the urethra, and
 (3) withdrawing the scope means while designating reference points by pressing selected computer keys,
(d) graphically displaying the urethral organs on the screen by drawing the organis on the screen in accordance with the memory data and computations performed,
(e) displaying a reference axis on the screen,
(f) resetting the first transducer to its initial reading,
(g) inserting the catheterizing means into the urethral organs, and
(h) displaying a graphic representation of the pressure applied to the catheterizing means and its position in the urethral organs in exact location to the urethral organs displayed along the reference axis.

12. A method of precise anatomical profilometry utilizing profile apparatus joined to a computer having a memory and video screen, said computer communicating with reference point fixing means and a catheterizing means, the steps comprising:
(a) fixing an anatomical reference point in the computer by said reference point fixing means in a selected anatomical region,
(b) displaying the region graphically while simultaneously displaying a reference axis on the screen,
(c) inserting the catheterizing means into the anatomical region,
(d) moving said catheterizing means in and out of the anatomical region, and
(e) graphically representing on the screen the pressure applied to the catheterizing means at exact locations during catheterizing means movement relative to the anatomical region displayed.

13. The method of claim 12 wherein the step of fixing an anatomical reference point comprises fixing said reference point with x-rays.

14. The method of claim 12 wherein the step of fixing an anatomical reference point comprises fixing said reference point with ultrasound.

* * * * *

UNITED STATES PATENT AND TRADEMARK OFFICE
CERTIFICATE OF CORRECTION

PATENT NO. : 4,825,875
DATED : 02 May 1989
INVENTOR(S) : Champil A. Ninan and Abraham C. Ninan It is certified that error appears in the above-identified patent and that said Letters Patent is hereby corrected as shown below:

On Page 1, the zip code for the inventors should be changed to:

-- 28311 --

Signed and Sealed this

Ninth Day of January, 1990

*Attest:*

JEFFREY M. SAMUELS

*Attesting Officer*     *Acting Commissioner of Patents and Trademarks*